United States Patent
Kraft et al.

(10) Patent No.: US 10,570,080 B2
(45) Date of Patent: Feb. 25, 2020

(54) PERFUME KETONES

(71) Applicant: Givaudan, S.A., Vernier (CH)

(72) Inventors: Philip Kraft, Dübendorf (CH); Roger Emter, Zurich (CH); Felix Flachsmann, Dübendorf (CH); Samuel Jordi, Oberägeri (CH); Andreas Natsch, Uetikon (CH)

(73) Assignee: GIVAUDAN S.A., Vernier (CH)

( * ) Notice: Subject to any disclaimer, the term of this patent is extended or adjusted under 35 U.S.C. 154(b) by 61 days.

(21) Appl. No.: 15/777,820

(22) PCT Filed: Dec. 8, 2016

(86) PCT No.: PCT/EP2016/080334
§ 371 (c)(1),
(2) Date: May 21, 2018

(87) PCT Pub. No.: WO2017/097938
PCT Pub. Date: Jun. 15, 2017

(65) Prior Publication Data
US 2018/0370890 A1   Dec. 27, 2018

(30) Foreign Application Priority Data
Dec. 9, 2015   (GB) .................................. 1521682.3

(51) Int. Cl.
*C11D 3/50* (2006.01)
*C07C 49/557* (2006.01)
*C11B 9/00* (2006.01)

(52) U.S. Cl.
CPC .......... *C07C 49/557* (2013.01); *C11B 9/0034* (2013.01); *C11B 9/0057* (2013.01);
(Continued)

(58) Field of Classification Search
CPC ... C07C 49/557; C11B 9/0034; C11B 9/0057; C11D 3/50
See application file for complete search history.

(56) References Cited

U.S. PATENT DOCUMENTS

| 3,931,323 A | 1/1976 | Büchi et al. |
| 4,198,309 A | 4/1980 | Mookherjee et al. |

(Continued)

FOREIGN PATENT DOCUMENTS

| EP | 1 162 190 A2 | 12/2001 |
| WO | WO 2008/151455 A1 | 12/2008 |
| WO | WO 2010/080504 A1 | 7/2010 |

OTHER PUBLICATIONS

PCT/EP2016/080334—International Search Report, dated Feb. 8, 2017.
(Continued)

*Primary Examiner* — John R Hardee
(74) *Attorney, Agent, or Firm* — Curatolo Sidoti Co., LPA; Joseph G. Curatolo; Salvatore A. Sidoti

(57) ABSTRACT

A compound of the formula (I)

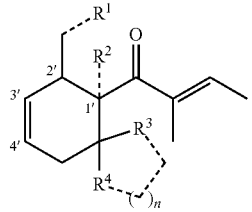

(I)

in which, independently,
$R_1$ is selected from H and methyl;
(Continued)

$R_2$ is selected from H, and methyl;
$R_3$ is selected from H, methyl and ethyl;
$R_4$ is selected from H, methyl and ethyl;
or $R_3$ and $R_4$ together form a ring in which n is 1 or 2.
The compounds have the characteristic desirable odour qualities of the Damascone® molecules, but lack their disadvantageous skin sensitization effects.

17 Claims, 2 Drawing Sheets

(52) U.S. Cl.
CPC ............ *C11D 3/50* (2013.01); *C07B 2200/07* (2013.01); *C07B 2200/09* (2013.01); *C07C 2601/16* (2017.05); *C07C 2602/50* (2017.05)

(56) References Cited

U.S. PATENT DOCUMENTS

| | | | |
|---|---|---|---|
| 4,226,892 A | 10/1980 | Kovats et al. | |
| 6,822,121 B2 | 11/2004 | Watanabe et al. | |
| 7,812,195 B2 * | 10/2010 | Granier | C07C 403/16 510/106 |
| 9,012,391 B2 | 4/2015 | Granier et al. | |
| 2002/0004615 A1 | 1/2002 | Watanabe et al. | |
| 2004/0087453 A1 * | 5/2004 | Dykstra | A61K 8/0229 510/101 |
| 2010/0179088 A1 * | 7/2010 | Flachsmann | A61K 8/46 510/499 |
| 2010/0292128 A1 | 11/2010 | Granier et al. | |

OTHER PUBLICATIONS

PCT/EP2016/080334—International Written Opinion, dated Feb. 8, 2017.

Roger Emter, et al., "Performance Of A Novel Keratinocyte-Based Reporter Cell Line To Screen Skin Sensitizers In Vitro", Toxicology and Applied Pharmacology, Jun. 15, 2010, vol. 245, Issue 3, pp. 281-290.

Andreas Natsch, et al., "LC-MS-Based Characterization of the Peptide Reactivity Of Chemicals To Improve The In Vitro Prediction Of The Skin Sensititzation Potential", Toxicological Sciences, Sep. 12, 2008, vol. 106, Issue 2, pp. 464-478.

* cited by examiner

PERFUME KETONES

CROSS REFERENCE TO RELATED APPLICATIONS

This application is a national stage application of International Application No. PCT/EP2016/080334, filed 8 Dec. 2016, which claims priority from Great Britain Patent Application No. 1521682.3, filed 9 Dec. 2015, which applications are incorporated herein by reference.

This disclosure relates to chemical compounds, their preparation and their use in perfumery.

The compounds (2E)-1-(2',6',6'-trimethylcyclohex-2'-en-1'-yl)but-2-en-1-one, (2E)-1-(2',6',6'-trimethylcyclohex-1'-en-1'-yl)but-2-en-1-one, (2E)-1-(2',6',6'-trimethylcyclohex-3'-en-1'-yl)but-2-en-1-one and (2E)-1-(2',6',6'-trimethylcyclohexa-1',3'-dien-1'-yl)but-2-en-1-one, commercially available as Damascone alpha™, Damascone beta™, Damascone delta™ and Damascenone™

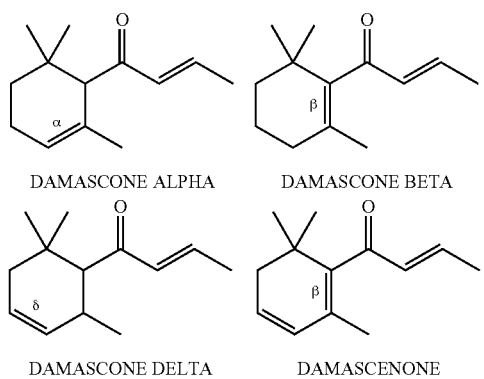

DAMASCONE ALPHA   DAMASCONE BETA

DAMASCONE DELTA   DAMASCENONE are highly desirable fragrance materials, especially where fruity or floral notes are desired. They are described, for example, in U.S. Pat. Nos. 4,198,309 and 4,226,892.

However, these materials have proved to be especially potent skin sensitizers, and this has severely restricted their uses, considerably confining their usefulness in both fine fragrances and consumer product perfume formulations.

It has now been surprisingly found that certain similar compounds with a 2-methyl substituent and a double bond in position C(3')=C(4') can deliver the same desirable natural complex fruity-floral dried-fruit odor but with reduced, or in some cases no, skin sensitization. There is therefore provided a compound of the Formula I

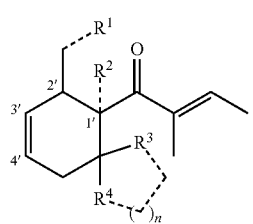

(I)

in which, independently,
$R^1$ is selected from H and methyl;
$R^2$ is selected from H, and methyl;
$R^3$ is selected from H, methyl and ethyl;
$R^4$ is selected from H, methyl and ethyl;
or $R^3$ and $R^4$ together form a ring in which n is 1 or 2.

Particularly significant is the fact that the central cyclohexenyl ring has a double bond at position 3', since only in this position the odor of the resulting compounds is not impeded by 2-methyl group, which is primarily responsible for blocking the sensitization potential of the enone substructure in the side chain. The prior art, for example, U.S. Pat. No. 4,226,892, describes a ring with a single double bond at either position 1' or position 2', or two conjugated double bonds at positions 1' and 3'. It has been surprisingly found that the use of the single double bond at position 3' allows for the introduction of a 2-methyl group that, in this combination, effectively removes the sensitization potential of the known molecules, while maintaining or even improving on their desirable odour qualities.

In a particular embodiment, $R^4$ is selected from methyl and ethyl. These compounds have less harsh and less herbaceous fruity-floral odour qualities devoid of aspects of Cyprisate™ (methyl 1,4-dimethylcyclo-hexanecarboxylate), thus providing more desirable fruity-floral notes closer to the Damascone™ compounds, but also lacking their skin sensitization problems.

There is therefore also provided a method of providing in a fragrance application a fruity-floral fragrance note with reduced skin sensitization, comprising the addition to a fragrance application base of a compound according to Formula I.

Sensitization is measured by the commercially-available and universally-accepted KeratinoSens™ test, which compares the potential skin sensitization risk of chemicals. It is recommended by EURL ECVAM (European Union Reference Laboratory for Alternatives to Animal Testing) for use within an integrated strategy for skin sensitisation testing. An OECD test guideline (Guideline for the Testing of Chemicals. In Vitro Skin Sensitisation: ARE-Nrf2 Luciferase Test Method) was released in February 2015.

The KeratinoSens™ cell line contains a stable insertion of a Luciferase gene under the control of the ARE-element of the gene AKR1C2 and induction of luciferase is indicative of skin sensitization potential (R. Emter, G. Ellis, A. Natsch, *Toxicol. Appl. Pharmacol.* 2010, 245, 281-290). The assay was performed as described by the OECD test guideline 442d. KeratinoSens cells were grown for 24 h in 96-well plates. The medium was then replaced with medium containing the test chemical and the solvent dimethylsulfoxide (DMSO) at a final level of 1%. Each compound was tested at 12 binary dilutions in the range from 0.98 to 2000 µM. Cells were incubated for 48 h with the test agents, and then luciferase activity and cytotoxicity were determined. This full procedure was repeated three times for each chemical. For each chemical in each repetition and at each concentration, the gene induction compared to DMSO controls and the wells with statistically significant induction over the threshold of 1.5 (i.e. 50% enhanced gene activity) were determined. Furthermore, the maximal fold-induction ($I_{max}$) and the EC1.5 value (concentration in µM for induction above the threshold) were calculated. Chemicals are rated as positive (i.e. likely skin-sensitizers) in the assay if the following three criteria are fulfilled:

(i) EC1.5 value is below 1000 µM
(ii) At the lowest concentration with a gene induction above 1.5 fold, the cellular viability is above 70%
(iii) There is an apparent overall dose-response for luciferase induction, which is similar between the repetitions.

The compounds of Formula I possess stereocentres in positions 1' and 2', and if $R^3$ differs from $R^4$, also in position 6'. They therefore exist in different diastereomeric and enantiomeric forms. In addition, the double bond in position 2 can be (E)- or (Z)-configured. The (2E,1'R*,2'S*)-diastereomers possess particularly low odor thresholds.

Particular examples of compounds of Formula I are those, in which both $R^1$ and $R^2$ are H. Of these, those in which $R^3$ and $R^4$ are methyl or together form a cyclopentyl ring (n=1) are especially preferred.

Further particular examples of compounds of Formula I are (2E,1'R*,2'S*)-2-methyl-1-(2',6',6'-trimethylcyclohex-3'-en-1'-yl)but-2-en-1-one, (2E,1'R*,2'R*)-2-methyl-1-(2',6',6'-trimethylcyclohex-3'-en-1'-yl)but-2-en-1-one, (2E,6'R*,7'S*)-2-methyl-1-(7'-methylspiro[4.5]dec-8'-en-6'-yl)but-2-en-1-one, (2E,6'R*,7'R*)-2-methyl-1-(7'-methylspiro[4.5]dec-8'-en-6'-yl)but-2-en-1-one, (2E)-1-(2',6'-dimethylcyclohex-3'-en-1'-yl)-2-methylbut-2-en-1-one, (2E)-1-(6'-ethyl-2'-methylcyclohex-3'-en-1'-yl)-2-methylbut-2-en-1-one, (2E)-2-methyl-1-(1',2',6'-trimethylcyclohex-3'-en-1'-yl)but-2-en-1-one, (2E,1'R*,2'S*)-2-methyl-1-(2'-methylcyclohex-3'-en-1'-yl)but-2-en-1-one, and (2E,1'R*,2'R*)-2-methyl-1-(2'-methylcyclohex-3'-en-1'-yl)but-2-en-1-one, a particular example being (2E,1'R*,2'S*)-2-methyl-1-(2',6',6'-trimethylcyclohex-3'-en-1'-yl)but-2-en-1-one.

Compounds of Formula I may be prepared by methylation of the corresponding but-2-en-1-ones in position 2 employing a strong base such as lithium diisopropylamide or lithium bis(trimethylsilyl)amide and a methylation agent such as a methyl halide, or from the corresponding esters itself, for instance available by Diels-Alder reactions of a 5-$R^1$-substituted (3E)-penta-1,3-diene with a corresponding α,(β-unsaturated ester and subsequent Grignard reaction of the resulting product with a 1-methyl-2-propenylmagnesium halide in the presence of a strong base such as lithium diisopropylamide to prevent further reaction to the carbinol by capturing the enolate form of the compounds of Formula I.

In a further embodiment, the compound of Formula I may be generated by means of a precursor, that is, a compound that, under particular conditions (for example, heat, light, chemical stimulation) will break down to form a compound of Formula I. This is particularly useful in some applications, such as laundry or hair care, as the compound can be generated in situ, when its presence is desired.

There is therefore also provided a precursor capable of generating a compound of the Formula I, the precursor being a compound of the Formula II

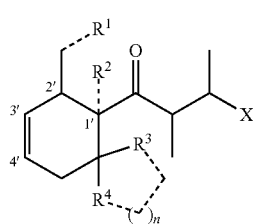

(II)

in which X is selected from $SR^5$, $NHR^6$ and $NR^6R^7$, $R^5$, $R^6$ and $R^7$ being selected from linear or branched $C_1$-$C_{15}$ alkyl, a $C_3$-$C_8$ cycloalkyl or an aryl substituent, the cycloalkyl and aryl being optionally substituted with linear or branched $C_1$-$C_7$ alkyl groups, or, in the case of $NR^6R^7$, $R^6$ and $R^7$, together with the nitrogen atom to which they are attached, form part of a polymeric entity;

There is therefore also provided a method of providing in a fragrance application a compound of Formula I as hereinabove described, comprising
(i) the preparation of a compound of Formula II
(ii) adding the compound of Formula II to an application; and
(iii) subjecting the application to conditions that will result in the generation of a compound of the Formula I.

There is further provided the use of a compound of Formula II in a fragrance application for the in situ generation of a compound according to Formula I.

In the case of polymeric entities, any such suitable entity is suitable, a typical example being a polyethylene imine. Such materials are readily available commercially, for example the Lupasol™ range of BASF.

Although compounds of the general type of Formula II are known, for example U.S. Pat. No. 4,226,892, it was not known that a particular subset of this group has this particular advantage.

The compound of Formula II, which may be prepared by any suitable method known to the art. The materials and conditions for such a preparation are well known to the art, and only routine, non-inventive experimentation is required to produce a suitable compound. In a typical, non-limiting example, a compound of Formula II may be prepared by the reaction of approximately equimolar amounts of a compound of formula I with one of $HSR^5$, $H_2NR^6$, $HNR^6R^7$, preferably at 20-80° C., either neat or in a solvent such as ethanol or toluene, optionally in the presence of an organic base, such as 1,8-diazabicyclo[5.4.0]undec-7-ene (0.5-1.5 equivalents), or an inorganic base, such as potassium carbonate. The product may be isolated by standard workup procedures known to the person skilled in the art of organic synthesis. The compound of Formula II may be used in crude form, or it may be purified by standard purification procedures, such as column chromatography or distillation.

The compounds of Formula I may be used in fragrance compositions, that is, compositions that provide desirable fragrance, either as stand-alone fragrance providers or incorporated into fragrance applications to provide them with a desirable fragrance. The compounds of Formula I may be used individually or in combination with one or more other compounds of Formula I. They may be combined in such fragrance compositions with any of the known range of commercially-available fragrance raw materials, either natural or synthetic, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, diluents, surfactants and other auxiliary agents commonly used in the art. Examples of suitable diluents include dipropylene glycol (DPG), isopropyl myristate (IPM), triethyl citrate (TEC) and alcohol (e.g. ethanol). These may be used in the normal proportions known to the art.

The following list comprises non-limiting examples of known odorant molecules, which may be combined with the compounds of Formula I:
  essential oils and extracts, e.g. agarwood oil (white and/or authentic), castoreum, costus root oil, oak moss absolute, geranium oil, tree moss absolute, basil oil, fruit oils, such as bergamot oil and mandarine oil, myrtle oil, palmarose oil, patchouli oil, petitgrain oil, jasmine oil, rose oil, sandalwood oil, wormwood oil, lavender oil or ylang-ylang oil;

alcohols, e.g. cinnamic alcohol, cis-3-hexenol, citronellol, Ebanol™, eugenol, farnesol, geraniol, Super Muguet™, linalool, menthol, nerol, phenylethyl alcohol, rhodinol, Sandalore™, terpineol or Timberol™;

aldehydes and ketones, e.g. Azurone® [7-(3-methylbutyl)-1,5-benzodioxepin-3-one], anisaldehyde, α-amyl-cinnamaldehyde, Cashmeran®, Georgywood™, Hedione®, hydroxycitronellal, Iso E Super®, Isoraldeine®, Kephalis™, Lilial®, maltol, methyl cedryl ketone, methylionone, verbenone, or vanillin, ether and acetals, e.g. Ambrox®, geranyl methyl ether, rose oxide, or Spirambrene®;

esters and lactones, e.g. benzyl acetate, cedryl acetate, γ-decalactone, Helvetolide®, γ-undecalactone or vetivenyl acetate;

macrocycles, e.g. Ambrettolide, ethylene brassylate or Exaltolide®; and heterocycles, e.g. isobutylchinoline.

The compounds according to formula (I) may be used in a broad range of fragrance applications, that is, products in which fragrance is desired. Such fragrance applications may be in any field of fine and functional perfumery, such as perfumes, air care products, household products, laundry products, body care products and cosmetics. Non-limiting examples of such products include textile treatment products, ironing aids, laundry detergents, laundry care products, fabric conditioners, cleaning products, in particular, for hard and/or soft surfaces, such as furniture and floor polishes general purpose cleaners, specific cleaners for kitchen and toilet use, disinfectants, room fragrancers and air fresheners, toilet blocks, hair care products, such as shampoos, colourants and conditioners, anti-mould and anti-fungal products, oral care products such as toothpastes, tooth gels and mouthwashes, cosmetics and pharmaceuticals.

Because of the reduced or even totally eliminated tendency for skin sensitisation, the compounds of Formula I are particularly effective in fragrance applications that will be in contact with the skin, either of short duration (cleaning materials) or long duration (cosmetics and pharmaceutical preparations).

The fragrance applications may be prepared by mixing the compounds, alone or as part of a fragrance composition, into a fragrance application base, that is, a composition comprising all the ingredients of the desired fragrance application apart from the perfume. These will naturally depend on the nature of the fragrance application but typical non-limiting examples well known to and used by the art include surfactants, detersive agents, abrasive agents, solvents, thinners and diluents, pigments, dyestuffs and other colouring matters, thickeners and rheology modifiers, disinfectants and antimicrobial compounds, extenders and fillers. The proportions that may be used are those well known to the art for each particular use and circumstance.

The compounds can be employed in widely varying amounts, depending upon the specific fragrance application and on the nature and quantity of other odorant ingredients. The proportion is typically from 0.1 to 10 weight percent of the application. In one embodiment, compounds of the present invention may be employed in a fabric softener in an amount of from 0.001 to 0.1 weight percent. In another embodiment, compounds of the present invention may be used in fine perfumery in amounts from 0.01 to 20 weight percent (e.g. up to about 10 weight percent), more preferably between 0.01 and 5 weight percent. However, these values are given only by way of example, since the experienced perfumer may also achieve effects or may create novel accords with lower or higher concentrations.

The compounds of Formula 1, of fragrance compositions incorporating them, may also be incorporated in perfumed products in entrapped form, that is, entrapped within a suitable entrapment material. Typical examples of entrapment well known to the art include polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like.

This disclosure is further described with reference to the following non-limiting examples and the accompanying drawings, which depict particular embodiments.

EXAMPLE 1

(2E,1'R*,2'S*)-2-Methyl-(2',6',6'-trimethylcyclohex-3'-en-1'-yl)but-2-en-1-one

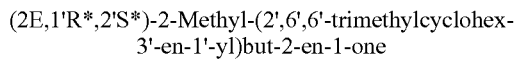

In a reaction flask, an LDA solution was prepared at −70° C. under N$_2$ atmosphere by dropwise addition of a 2.5 M solution of nBuLi in hexanes (35.8 mL, 90 mmol) to a stirred solution of iPr$_2$NH (12.9 mL, 90 mmol) in anhydrous THF (50 mL). After stirring for 10 min at this temp., the cooling bath was removed, and the reaction mixture was allowed to warm to room temp. within 45 min. At this temp., a 0.5 M solution of 1-methyl-2-propenylmagnesium chloride in THF (244 mL, 122 mmol) was added dropwise with stirring over a period of 3 h, followed by dropwise addition of a solution of (1R*,2S*)-methyl 2,6,6-trimethylcyclohex-3-enecarboxylate (15.0 g, 81.0 mmol) in dry THF (150 mL) over a period of 1 h 30 min. The resulting reaction mixture was heated to 40° C., and stirring was continued at this temp. for 18 h. The reaction mixture was allowed to cool down to room temp., and poured into ice-cold 2 M aqueous NaOH solution (250 mL) with vigorous stirring. After stirring for 45 min., the mixture was extracted with Et$_2$O (2×300 mL), and the organic extracts were washed with water (2×250 mL) and brine (1×200 mL). The combined organic extracts were dried over Na$_2$SO$_4$, filtered, and concentrated under reduced pressure. Flash chromatography (600 g silica gel, pentane-ether, 39:1; R$_f$=0.41) of the resulting residue afforded a 5:1 mixture of the desired (2E,1'R*,2'S*)-2-methyl-1-(2',6',6'-trimethylcyclohex-3'-en-1'-yl)but-2-en-1-one/(3Z,1R*,2S*)-1-(2,6,6-trimethylcyclohex-3-en-1-yl)pent-3-en-1-one and the starting material (11.7 g) as a yellowish liquid. Since the (3Z,1R*,2S*)-1-(2,6,6-trimethylcyclohex-3-en-1-yl)pent-3-en-1-one isomer proved to be very weak in smell, not altering the character of the main product (2E,1'R*,2'S*)-2-methyl-1-(2',6',6'-trimethylcyclohex-3'-en-1'-yl)but-2-en-1-one, only the starting material was removed by Kugelrohr distillation to afford a 5:1 mixture of (2E,1'R*,2'S*)-2-methyl-1-(2',6',6'-trimethylcyclohex-3'-en-1'-yl)but-2-en-1-one/(3Z,1R*,2S*)-1-(2,6,6-trimethylcyclohex-3-en-1-yl)pent-3-en-1-one (8.70 g,48%) as a colourless odoriferous liquid.

Spectral data for the main component (2E,1'R*,2'S*)-2-methyl-1-(2',6',6'-trimethylcyclohex-3'-en-1'-yl)but-2-en-1-one: IR (neat): 3018, 2956, 1656, 1640, 1458, 1367, 1273, 1233, 1078, 688 cm$^{-1}$. $^1$H NMR (CDCl$_3$): δ=0.79/0.94 (2s, 6H, —CMe$_2$-), 0.80 (d, J=7.0 Hz, 3 H, CHCH$_3$), 1.71 (m$_c$, 1 H, —CMe$_2$-CHH—), 1.79 (quint, J=1.0 Hz, 3 H, CO—CMe=CHMe), 1.85 (dq, J=7.0, 1.0 Hz, 3 H, CO—CMe=CHMe), 1.99 (m$_c$, 1 H, CMe$_2$-CHH—), 2.27 (m$_c$, 1 H, =CH—CHMe-CH(CMe$_2$)-CO), 2.94 (d, J=10.5 Hz, 1 H, —CHMe-CH(CMe$_2$)-CO, trans), 5.47-5.55 (m, 2

H, —CH═CH—), 6.69 (q, J=7.0 Hz, 1 H, —CMe═CHMe) ppm. $^{13}$C NMR (CDCl$_3$): δ=11.2 (q), 14.9 (q), 20.0 (q), 20.6 (q), 29.9 (q), 31.9 (d), 33.3 (s), 42.1 (t), 54.7 (d), 124.0 (d), 132.5 (d), 136.3 (d), 141.7 (s), 205.8 (s) ppm. MS: m/z (%)=29 (9), 41 (10), 55 (35), 83 (100), 123 (8), 191 (3), 206 (5) [M$^+$].

Odour description: fruity-floral, typical damascone, dried fruits, sweet, plum, milky, apple.

EXAMPLE 2

(2E,1'R*,2'R*)-2-Methyl-1-(2',6',6'-trimethylcyclohex-3'-en-1'-yl)but-2-en-1-one At −30° C. under N$_2$ atmosphere, a solution of (2E,1'R*,2'R*)-1-(2,6,6-trimethylcyclohex-3-en-1-yl)but-2-en-1-one (2.00 g, 10.4 mmol) in THF (15 mL), prepared by Diels-Alder reaction of 4-methylpent-3-en-2-one and (3E)-penta-1,3-diene according to EP 1 162 190 A2 with subsequent aldol condensation with acetaldehyde according to WO 2010/080504 A1, was added over a period of 35 min. to a stirred 1.0 M solution of LiHMDS in THF (15.6 mL, 15.6 mmol). After keepin the stirred reaction mixture between −30° C. and −10° C. for 30 min, neat MeI (0.975 mL, 15.6 mmol) was added dropwise at −20° C. during a period of 20 min. After stirring at −20° C. for 10 min, the reaction mixture was allowed to warm to room temp., and the mixture was stirred for 18 h at this temp. The reaction mixture was poured into ice-cold satd. NH$_4$Cl-solution (80 mL), and then extracted with diethyl ether (2×100 mL). The combined organic extracts were washed with water (1×100 mL) and brine (1×50 mL), and then dried over Na$_2$SO$_4$, filtered and concentrated under reduced pressure. Purification of the crude product by flash chromatography (150 g silica gel, pentane-ether, 39:1; R$_f$=0.32) and Kugelrohr distillation afforded the title compound (2E,1'R*,2'R*)-2-methyl-1-(2',6',6'-trimethylcyclohex-3'-en-1'-yl)but-2-en-1-one (1.00 g, 40%) as a colourless crystals (mp: 31.5-33.5° C.).

IR (neat): 3017, 2956, 2873, 1661, 1639, 1459, 1391, 1269, 1235 1067, 1014, 653 cm$^{-1}$. $^1$H NMR (CDCl$_3$): δ=0.82/0.99 (2s, 6 H, —CMe$_2$-), 0.86 (d, J=7.0 Hz, 3 H, CHCH$_3$), 1.57-1.71 (m, 1 H, —CMe$_2$-CHH—), 1.76 (s, 3 H, CO—CMe═CHMe), 1.86 (d, J=7.0 Hz, 3 H, CO—CMe═CHMe), 2.06-2.29 (m, 1 H, —CMe$_2$-CHH), 2.53 (m$_c$, 1 H, ═CH—CHMe-CH(CMe$_2$)—CO), 3.28 (d, J=6.5 Hz, 1 H, —CHMe-CH(CMe$_2$)-CO, cis), 5.32-5.48 (m, 1 H, —CH═CH—), 5.71 (ddt, J=10.0, 5.0, 2.5 Hz, 1 H, —CH═CH—), 6.69 (q, J=7.0 Hz, 1 H, —CMe═CHMe) ppm. $^{13}$C NMR (CDCl$_3$): δ=11.0 (q), 14.9 (q), 17.7 (q), 28.7 (q), 29.1 (q), 30.7 (d), 32.4 (s), 36.0 (t), 50.8 (d), 125.7 (d), 128.9 (d), 135.8 (d), 142.0 (s), 205.1 (s) ppm. MS: m/z (%)=29 (19), 41 (23), 55 (70), 83 (100), 123 (43), 137 (33), 151 (14), 163 (6), 177 (3), 191 (8), 206 (9) [M$^+$].

Odour description: Minty, agrestic, fruity-floral, damascone-like.

EXAMPLE 3

(2E,6'R*,7'S*)-2-Methyl-1-(7'-methylspiro[4.5]dec-8'-en-6'-yl)but-2-en-1-one and (2E,6'R*,7'R*)-2-Methyl-1-(7'-methylspiro[4.5]dec-8'-en-6'-yl)but-2-en-1-one In a reacition flask at −70° C. under N$_2$ atmosphere, an LDA solution was prepared by dropwise addition of a 2.5 M solution of nBuLi in hexanes (9.70 mL, 24.2 mmol) to a stirred solution of iPr$_2$NH (3.44 mL, 24.2 mmol) in anhydrous THF (15 mL). After stirring for 10 min at −70° C., the cooling bath was removed and the reaction mixture allowed to warm to room temp. within 30 min. Then, at room temp., a 0.5 M solution of 1-methyl-2-propenylmagnesium chloride in THF (66.1 mL, 33.1 mmol) was added dropwise over a period of 1 h, followed by dropwise addition during a period of 1 h of a solution of (6'R*,7'S*)-ethyl 7-methylspiro [4.5]dec-8-ene-6-carboxylate (5.00 g, 22.0 mmol) in dry THF (45 mL), prepared according to WO 2008151455 A1. The resulting reaction mixture was heated to 40° C., and the mixture stirred at this temp. for 18 h. The heating source was removed, and after the reaction mixture had reached room temp., it was poured into ice-cold 2 M NaOH-solution (100 mL), and stirred vigorously for 45 min. The product was extracted with diethyl ether (2×200 mL), and the organic extracts were washed with water (2×200 mL) and brine (1×150 mL). The combined organic extracts were dried over Na$_2$SO$_4$, filtered and concentrated under reduced pressure, to provide a mixture of the crude title compounds, which were then separated and purified by flash chromatography (300 g silica gel, pentane-ether, 39:1; R$_f$=0.67 (trans), R$_f$=0.48 (cis)) followed by Kugelrohr distillation to provide (2E,6'R*,7'S*)-2-methyl-1-(7'-methylspiro[4.5]dec-8'-en-6'-yl)but-2-en-1-one (650 mg, 12%) as a colourless liquid, and (2E,6'R*,7'R*)-2-methyl-1-(7'-methylspiro[4.5]dec-8'-en-6'-yl)but-2-en-1-one (900 mg, 17%) as colorless crystals (mp: 49.2-52.0° C.).

Spectroscopic data for (2E,6'R*,7'S*)-2-methyl-1-(7'-methylspiro[4.5]dec-8'-en-6'-yl)but-2-en-1-one: IR (neat): 3014, 2954, 1656, 1639, 1234, 1075, 688 cm$^{-1}$. $^1$H NMR (CDCl$_3$): δ=0.82 (d, J=7.0 Hz, 3 H, CH$_3$), 0.90-1.66 (m, 8 H, CH$_2$), 1.81 (quint, J=1.0 Hz, 3 H, CO—CMe═CHMe), 1.88 (dq, J=7.0, 1.0 Hz, 3 H, CO—CMe═CHMe), 1.89-2.07 (m, 2H, CH$_2$), 2.64 (m$_c$, 1 H, ═CH—CHMe-CH—CO), 3.16 (d, J=10.5 Hz, 1 H, —CHMe-CH—CO, trans), 5.49-5.59 (m, 2 H, —CH═CH—), 6.72 (qd, J=7.0, 1.0 Hz, 1 H, —CMe═CHMe) ppm. $^{13}$C NMR (CDCl$_3$): δ=11.2 (q), 15.0 (q), 20.0 (q), 23.7 (t), 24.5 (t), 29.6 (t), 33.2 (d), 38.8 (t), 39.7 (t), 45.3 (s), 52.8 (d), 124.3 (d), 133.6 (d), 136.7 (d), 141.7 (s), 206.1 (s) ppm. MS: m/z (%)=29 (10), 41 (12), 55 (39), 83 (100), 134 (16), 149 (19), 164 (4), 217 (3), 232 (5) [M$^+$].

Odour description for (2E,6'R*,7'S*)-2-methyl-1-(7'-methylspiro[4.5]dec-8'-en-6'-yl)but-2-en-1-one: rather weak, fruity-floral, apricot, peach, slight damascone aspect.

Spectroscopic data for (2E,6'R*,7'R*)-2-methyl-1-(7'-methylspiro[4.5]dec-8'-en-6'-yl)but-2-en-1-one): IR (neat): 3014, 2954, 1650, 1637, 1244, 1067, 657 cm$^{-1}$. $^1$H NMR (CDCl$_3$): δ=0.87 (d, J=7.5 Hz, 3 H, CH$_3$), 1.19-1.71 (m, 8 H, CH$_2$), 1.77 (quint, J=1.0 Hz, 3 H, CO—CMe═CHMe), 1.78-1.84 (m, 1 H, CH$_2$), 1.87 (dq, J=7.0, 1.0 Hz, 3 H, CO—Me═CHMe), 2.18-2.25 (m, 1 H, CH$_2$), 2.54 (m$_c$, 1 H, ═CH—CHMe-CH—CO) 3.32 (d, J=6.5 Hz, 1 H, —CHMe-CH—CO, cis), 5.41-5.41 (m, 1 H, —H═CH—) 5.69-5.73 (m, 1 H, —CH═CH—), 6.68 (qd, J=7.0, 1.0 Hz, 1 H, —CMe═CHMe) ppm. $^{13}$C NMR (CDCl$_3$): δ=11.1 (q), 14.9 (q), 17.9 (q), 23.4 (t), 24.2 (t), 31.6 (d), 33.9 (t), 38.5 (t), 39.1 (t), 44.3 (s), 50.7 (d), 126.0 (d), 129.8 (d), 135.7 (d), 142.1 (s), 204.8 (s) ppm. MS: m/z (%)=29 (22), 41 (27), 55 (87), 83 (100), 134 (30), 149 (51), 164 (17), 217 (7), 232 (13) [M$^+$].

Odour description for (2E,6'R*,7'R*)-2-methyl-1-(7'-methylspiro[4.5]dec-8'-en-6'-yl)but-2-en-1-one): fresh fruity, minty, damascenone.

EXAMPLE 4

(2E)-1-(2',6'-Dimethylcyclohex-3'-en-1'-yl)-2-methylbut-2-en-1-one as isomeric mixture In an autoclave, a mixture of methyl crotonate (7.00 g, 68.5 mmol) and (3E)-penta-1,3-diene (9.33 g, 137 mmol) was heated to 160° C., and stirred for 65 h. Purification of the crude product by flash chromatography (500 g silica gel, pentane-ether, 39:1; $R_f$=0.24) afforded methyl 2,6-dimethylcyclohex-3-enecarboxylate (4.20 g, 31%) as a colourless liquid. At room temp. under $N_2$ atmosphere, a 0.5 M solution of 1-methyl-2-propenylmagnesium chloride in THF (89.0 mL, 44.6 mmol) was added dropwise over a period of 1 h 30 min to a stirred 2.0 M LDA solution in THF (16.4 mL, 32.7 mmol). Followed by dropwise addition during a period of 1 h of a solution of the above prepared 2,6-dimethylcyclohex-3-enecarboxylate (5.00 g, 29.7 mmol) in THF (50 mL). The resulting reaction mixture was heated to 40° C., and the mixture stirred at this temp. for 18 h. The heating source was removed, and after the reaction mixture had reached room temp., it was poured into ice-cold 2 M NaOH-solution (150 mL). After vigorous stirring for 45 min, the product was extracted with diethyl ether (2×100 mL), and the organic extracts were washed with water (2×100 mL) and brine (1×100 mL). The combined organic extracts were dried over $Na_2SO_4$, filtered, and concentrated under reduced pressure. Purification of the resulting residue by flash chromatography (200 g silica gel, pentane-ether, 39:1; $R_f$=0.27) and Kugelrohr distillation afforded the title compound (2E)-1-(2',6'-dimethylcyclohex-3'-en-1'-yl)-2-methylbut-2-en-1-one (2.00 g, 31%) as liquid colourless mixture of isomers.

IR (neat): 3019, 2957, 1656, 1640, 1374, 1232, 1070, 684 cm$^{-1}$. $^1$H NMR (CDCl$_3$): δ=0.74 (d, J=6.5 Hz, 1 H, CH$_3$), 0.75 (d, J=6.5 Hz, 2 H, CH$_3$), 0.81 (d, J=7.0 Hz, 2.2 H, CH$_3$), 0.84 (d, J=6.5 Hz, 0.8 H, CH$_3$), 1.61-1.65 (m, 0.2 H, cyclohexane ring), 1.67-1.77 (m, 0.8 H, cyclohexane ring), 1.77-1.80 (m, 1 H, CH$_3$), 1.82 (quint, J=1.0 Hz, 2 H, CH$_3$), 1.84-1.87 (m, 1 H, CH$_3$), 1.89 (dq, J=7.0, 1.0 Hz, 2 H, CH$_3$), 1.91-1.99 (m, 0.6 H, cyclohexane ring), 1.99-2.20 (m, 1.4 H, cyclohexane ring), 2.36-2.44 (m, 0.3 H, cyclohexane ring), 2.45-2.56 (m, 0.7 H, cyclohexane ring), 2.72 (t, J=10.0 Hz, 0.6 H, cyclohexane ring), 3.13-3.28 (m, 0.4 H, cyclohexane ring), 5.49 (dq, J=10.0, 2.0 Hz, 0.6 H, endocyclic-CH=CH—), 5.57-5.66 (m, 1.4 H, endocyclic-CH=CH—), 6.69-6.81 (m, 1 H, —CH=CH—) ppm. $^{13}$C NMR (CDCl$_3$), two main diastereomers: δ=11.0 (q), 14.8 (q), 15.0 (q), 17.1 (q), 19.7 (q), 20.1 (q), 24.5 (d), 32.8 (d), 32.9 (d), 33.9 (t), 34.3 (t), 35.3 (d), 50.3 (d), 53.2 (d), 125.0 (d), 125.2 (d), 131.9 (d), 132.9 (d), 136.2 (d), 137.5 (d), 138.8 (s), 141.4 (s), 203.1 (s), 207.2 (s) ppm. MS: m/z (%)=29 (8), 39 (11), 55 (46), 83 (100), 93 (8), 108 (8), 109 (8), 135 (4), 137 (4), 177 (4), 192 (5) [M$^+$].

Odour description: fruity-rosy, minty-agrestic, damascone-like.

EXAMPLE 5

(2E)-1-(6'-Ethyl-2'-methylcyclohex-3'-en-1'-yl)-2-methylbut-2-en-1-one as Isomeric Mixture In an autoclave, a mixture of methyl trans-2-pentenoate (6.00 g, 52.6 mmol) and (3E)-penta-1,3-diene (7.16 g, 105 mmol) was heated with stirring to 150° C. for 48 h. Purification of the crude product by flash chromatography (500 g silica gel, pentane-ether, 39:1; $R_f$=0.31) afforded methyl 6-ethyl-2-methylcyclohex-3-enecarboxylate (1.16 g, 12%) as a colourless liquid.

At room temp. under $N_2$ atmosphere, a 0.5 M solution of 1-methyl-2-propenylmagnesium chloride in THF (43.5 mL, 21.7 mmol) was added dropwise over a period of 1 h to a stirred 2.0 M LDA-solution in THF (7.97 mL, 15.93 mmol). A solution of the above prepared methyl 6-ethyl-2-methylcyclohex-3-enecarboxylate (2.64 g, 14.48 mmol) in THF (30 mL) was then added dropwise over a period of 1 h. The resulting reaction mixture was heated with stirring to 40° C. for 18 h. The heating source was removed, and after the reaction mixture had reached room temp., it was poured into ice-cold 2 M NaOH-solution (150 mL). After vigorous stirring for 45 min, the product was extracted with diethyl ether (2×100 mL), and the organic extracts were washed with water (2×100 mL) and brine (1×100 mL). The combined organic extracts were dried over $Na_2SO_4$, filtered, and concentrated under reduced pressure. Purification of the resulting residue by flash chromatography (280 g silica gel, pentane-ether, 39:1; $R_f$=0.35) and Kugelrohr distillation afforded the title compound (2E)-1-(6'-ethyl-2'-methylcyclohex-3'-en-1'-yl)-2-methylbut-2-en-1-one (480 mg, 15%) as liquid yellowish isomeric mixture.

IR (neat): 3018, 2961, 1656, 1640, 1374, 1231, 1067, 712, 685, 644 cm$^{-1}$. $^1$H NMR (CDCl$_3$): δ=0.76 (d, J=7.0 Hz, 1 H, CH$_3$), 0.78-0.85 (4 d, 5 H, CH$_3$), 0.86-1.12 (m, 2H, CH$_2$), 1.25 (ddd, J=13.0, 7.5, 3.5 Hz, 0.6 H, cyclohexane ring), 1.42-1.57 (m, 0.4 H, cyclohexane ring), 1.60-1.75 (m, 1 H, cyclohexane ring), 1.78-1.80 (m, 1 H, CH$_3$), 1.81-1.84 (m, 2 H, CH$_3$), 1.86 (dq, J=7.0, 1.0 Hz, 1 H, CH$_3$), 1.87-1.92 (m, 2 H, CH$_3$), 2.18-2.58 (series of m, 2 H, cyclohexane ring), 2.80 (t, J=10.0 Hz, 0.6 H, cyclohexane ring), 3.14-3.25 (m, 0.5 H, cyclohexane ring), 3.30 (dd, J=11.0, 5.5 Hz, 0.3 H, cyclohexane ring), 5.49 (dq, J=10.0, 2.0 Hz, 0.6 H, endocyclic-CH=CH—), 5.58-5.72 (m, 1.4 H, endocyclic-CH=CH), 6.68-6.84 (m, 1 H, —CH=CH—) ppm. $^{13}$C NMR (CDCl$_3$), two main diastereomers: δ=10.6 (q), 11.0 (q), 11.1 (q), 11.2 (q), 14.8 (q), 15.0 (q), 17.2 (q), 20.1 (q), 26.5 (t), 27.1 (t), 30.1 (t), 30.5 (d), 30.6 (t), 32.7 (d), 35.5 (d), 39.1 (d), 48.2 (d), 52.5 (d), 124.9 (d), 125.1 (d), 131.8 (d), 132.9 (d), 136.0 (d), 137.6 (d), 138.8 (s), 141.4 (s), 203.3 (s), 207.6 (s) ppm. MS: m/z (%)=29 (9), 41 (8), 55 (39), 83 (100), 93 (9), 122 (6), 137 (4), 177 (1), 192 (2), 206 (2, [M$^+$].

Odour description: fruity-floral, apple, slightly aromatic, in direction of Damascone alpha™.

EXAMPLE 6

(2E,1'R*,2'S*,6'S*)-2-Methyl-1-(1',2',6'-trimethylcyclohex-3'-en-1'-yl)but-2-en-1-one as Isomeric Mixture In an autoclave, a mixture of ethyl tiglate (7.00 g, 53.5 mmol) and (3E)-penta-1,3-diene (8.02 g, 118 mmol) was heated with stirring to 170° C. for 72 h. Purification of the crude product by flash chromatography (600 g silica gel, pentane-ether, 39:1; $R_f$=0.33) afforded ethyl 1,2,6-trimethylcyclohex-3-enecarboxylate (1.6 g, 15%) as a colourless liquid.

In a reaction flask at −70° C. under $N_2$ atmosphere, an LDA solution was prepared by dropwise addition of a 2.5 M solution of nBuLi in hexanes (6.66 mL, 16.6 mmol) to a stirred solution of iPr$_2$NH (2.34 mL, 16.6 mmol) in anhydrous THF (10 mL). After stirring for 10 min at −70° C., the cooling bath was removed, and the reaction mixture allowed to warm to room temp. within 30 min. At room temp., a 0.5

M solution of 1-methyl-2-propenylmagnesium chloride in THF (45.4 mL, 22.70 mmol) was then added dropwise with stirring over a period of 2 h, followed by dropwise addition during a period of 45 min of a solution of ethyl 1,2,6-trimethylcyclohex-3-enecarboxylate (3.00 g, 15.1 mmol) in dry THF (20 mL).

The resulting reaction mixture was heated with stirring to 40° C. for 18 h. The heating source was removed, and after the reaction mixture had reached room temp., it was poured into ice-cold 2 M NaOH-solution (100 mL). After vigorous stirring for 45 min, the product was extracted with diethyl ether (2×150 mL), and the organic extracts were washed with water (2×150 mL) and brine (1×100 mL). The combined organic extracts were dried over $Na_2SO_4$, filtered, and concentrated under reduced pressure. Purification of the resulting residue by flash chromatography (300 g silica gel, pentane-ether, 39:1; $R_f$=0.35) and Kugelrohr distillation afforded the (2E,1'R*,2'S*,6'S*)-configured title compound 2-methyl-1-(1',2',6'-trimethylcyclohex-3'-en-1'-yl)but-2-en-1-one as the main component (60%) of a liquid clolourless isomeric mixture (130 mg, 4%).

IR (neat): 3020, 2962, 2931, 1702, 1659, 1451, 1374, 1249, 1035, 1007, 979, 713, 605, 541 cm$^{-1}$. $^1$H NMR ($C_6D_6$), major component: δ=0.88 (d, J=6.5 Hz, 3 H, $CH_3$), 0.95 (d, J=7.0 Hz, 3 H, $CH_3$), 1.11 (s, 3 H, $CH_3$), 1.40 (dq, J=7.0, 1.0 Hz, 3 H, $CH_3$), 1.54 (dd, J=19.5, 11.0 Hz, 1 H, $CH_aH_b$), 1.70 (quint, J=1.0 Hz, 3 H, $CH_3$), 1.93 (ddd, J=19.5, 6.0, 3.0 Hz, 1 H, $CH_aH_b$), 2.17 (qt, J=7.0, 3.0 Hz, 1 H, CH—$C_3$), 2.56 (dquint, J=11.0, 6.5, 6.5, 6.5, 6.5 Hz, 1 H, $CH_2$—CH—$CH_3$), 5.50-5.52 (m, 2 H, 2× =CH—$CH_2$), 5.85 (qq, J=7.0, 1.5 Hz, 1 H, =CH—$CH_3$) ppm. $^{13}$C NMR ($C_6D_6$), major component: δ=13.4 (q), 13.7 (q), 17.3 (2q), 18.8 (q), 27.3 (d), 31.9 (t), 40.4 (s), 52.2 (s), 125.0 (d), 127.1 (d), 130.5 (d), 139.3 (s), 208.2 (s). MS: m/z (%)=29 (10), 41 (13), 55 (45), 83 (100), 91 (13), 107 (20), 122 (21), 123 (69), 139 (4), 151 (3), 177 (1), 191 (2), 206 (6, [M$^{+]}$).

Odour description: red fruits, raspberry, green-fruity, with a bell pepper nuance and rooty facets.

EXAMPLE 7

2E,1'R*,2'S*)-2-Methyl-1-(2'-methylcyclohex-3'-en-1'-yl)but-2-en-1-one

At room temp., a solution of ethyl acrylate (80.0 g, 799 mmol) in toluene (100 mL) was added dropwise to a a stirred suspension of aluminium trichloride (15.98 g, 120 mmol) and toluene (150 mL). After the addition the reaction mixture was stirred for 20 min at room temp., followed by dropwise addition of a solution of (3E)-penta-1,3-diene (82.0 g, 1199 mmol) in toluene (100 mL). The temp. was maintained between 25° C. and 36° C. by immersion in a water bath, and stirring was then continued for further 24 h at room temp.

The reaction mixture was poured into ice-cold 2 M HCl-solution (200 mL), and the product was extracted with hexane (2×200 mL). The organic extracts were washed with water (1×200 mL) and brine (1×200 mL), combined organic and were dried with $MgSO_4$, filtered, and concentrated under reduced pressure. Purification of the resulting residue by thin-film distillation (120° C./0.20 mbar), followed by disillation employing a Sulzer columm under high vacuo afforded (1R*,2S*)-ethyl 2-methylcyclohex-3-enecarboxylate (46.1 g, 34%) as colorless liquid.

At −70° C. under $N_2$ atmosphere, an LDA solution was prepared in a reacition flask by dropwise addition of a 2.5 M solution of nBuLi in hexanes (12.7 mL, 31.7 mmol) to a stirred solution of $iPr_2NH$ (4.5 mL, 31.7 mmol) in anhydrous THF (15 mL). After stirring for 10 min at −70° C., the cooling bath was removed, and the reaction mixture allowed to warm to room temp. over a period of 30 min. At room temp., a 0.5 M solution of 1-methyl-2-propenylmagnesium chloride in THF (86.0 mL, 43.2 mmol) was then added dropwise over a period of 2 h, followed by dropwise addition during a period of 1 h of a solution of (1R*,2S*)-ethyl 2-methylcyclohex-3-enecarboxylate (5.00 g, 28.8 mmol) in dry THF (45 mL), as prepared above. The resulting reaction mixture was heated to 40° C., and stirred at this temp. for 18 h. The heating source was removed, and the reaction mixture, after it had reached room temp., poured into ice-cold 2 M NaOH-solution (100 mL). After stirring vigorously for 45 min., the product was extracted with diethyl ether (2×200 mL), and the organic extracts were washed with water (2×200 mL) and brine (1×150 mL). The combined organic extracts were dried with $Na_2SO_4$, filtered and concentrated under reduced pressure. Purification of the resulting residue by flash chromatography (300 g silica gel, pentane-ether, 39:1; $R_f$=0.19) and Kugelrohr distillation afforded the title compound (2E,1'R*,2'S*)-2-Methyl-1-(2'-methylcyclohex-3'-en-1'-yl)but-2-en-1-one (1.00 g, 17%) as a colourless liquid.

IR (neat): 3018, 2961, 2912, 2837, 1661, 1643, 1434, 1393, 1371, 1298, 1273, 1242, 1095, 1060, 987, 868, 811, 730, 705, 636 cm$^{-1}$. $^1$H NMR (CDCl$_3$): δ=0.73 (d, J=7.0 Hz, 3 H, $CH_3$), 1.56-1.65 (m, 1 H, $CH_aH_b$), 1.74-1.84 (m, 1 H, $CH_aH_b$), 1.79 (quint, J=1.0 Hz, 3 H, $CH_3$), 1.87 (dq, J=7.0, 1.0 Hz, 3 H, $CH_3$), 1.93-2.14 (m, 2 H, =CH—$CH_2$—$CH_2$), 2.48-2.56 (m, 1 H, CH—CH—C=O), 3.35 (ddd, J=12.0, 5.5, 3.0 Hz, 1 H, CH—CH—C=O), 5.60-5.69 (m$_3$), 5.60-5.69 (m, 2 H, 2× =CH—$CH_2$), 6.72 (qq, J=7.0, 2.5 Hz, 1 H, =CH—$CH_3$) ppm. $^{13}$C NMR (CDCl$_3$): δ=11.2 (q), 14.8 (q), 16.2 (q), 19.1 (t), 25.1 (t), 33.1 (d), 44.2 (d), 126.2 (d), 132.1 (d), 136.3 (d), 137.7 (s), 204.3 (s) ppm. MS: m/z (%)=29 (15), 39 (20), 55 (75), 67 (13), 79 (16), 83 (100), 95 (14), 110 (8), 111 (9), 123 (13), 137 (5), 145 (2), 149 (3), 163 (16), 178 (5, [M$^+$]).

Odour description: agrestic, dark fruity, berries, plum, Cyprisate (methyl 1,4-dimethylcyclohexanecarboxylate).

EXAMPLE 8

(2E,1'R*,2'R*)-2-Methyl-1-(2'-methylcyclohex-3'-en-1'-yl)but-2-en-1-one

At room temp., a reaction flask was charged with ethanol (200 mL) and sodium (2.49 g, 108 mmol), and the resulting mixture was heated to reflux until all sodium was completely dissolved. (1R*,2S*)-Ethyl 2-methylcyclohex-3-enecarboxylate (91.0 g, 541 mmol), prepared by Diels-Alder reaction of ethyl acrylate and (3E)-penta-1,3-diene according to Example 7, was then added with stirring. After the reaction mixture had been stirred at reflux for 15 h, a second portion of sodium (1.24 g, 53.9 mmol) was added, and refluxing was continued for a further 3 h. The reaction mixture was allowed to cool to room temp., and the solvent was evaporated in a rotary evaporator. The resulting residue was taken up in 2-methoxy-2-methylpropan, washed with water (1×150 mL) and brine (1×150 mL), and then dried over $MgSO_4$. After filtration and removal of the solvent under reduced pressure, purification of the crude material by distillation in vacuo afforded (1R*,2R*)-ethyl 2-methylcyclohex-3-enecarboxylate (26.8 g, 29%) as colorless liquid.

In a reaction flask at −70° C. under $N_2$ atmosphere, an LDA solution was prepared by dropwise addition of a 2.5 M solution of nBuLi in hexanes (12.68 mL, 31.7 mmol) to a stirred solution of iPr$_2$NH (4.5 mL, 31.7 mmol) in anhydrous THF (15 mL). After stirring for 10 min at −70° C., the cooling bath was removed and the reaction mixture allowed to warm to room temp. within 30 min. Then, at room temp., a 0.5 M solution of 1-methyl-2-propenylmagnesium chloride in THF (86.0 mL, 43.2 mmol) was added dropwise over a period of 1 h, followed by dropwise addition during a period of 2 h of a solution of (1R*,2R*-ethyl 2-methylcyclohex-3-enecarboxylate (5.00 g, 28.8 mmol) in dry THF (45 mL) as prepared above. The resulting reaction mixture was heated to 40° C., and the mixture stirred at this temp. for 18 h. The heating source was removed, and after the reaction mixture had reached room temp., it was poured into ice-cold 2 M NaOH-solution (100 mL), and stirred vigorously for 45 min. The product was extracted with diethyl ether (2×200 mL), and the organic extracts were washed with water (2×200 mL) and brine (1×150 mL). The combined organic extracts were dried with Na$_2$SO$_4$, filtered and concentrated under reduced pressure. Purification of the crude product by flash chromatography (300 g silica gel, pentane-ether, 39:1; R$_f$=0.48) and Kugelrohr distillation afforded the title compound (2E,1'R*,2'R*)-2-methyl-1-(2'-methylcyclohex-3'-en-1'-yl)but-2-en-1-one (1.60 g, 30%) as a colourless liquid.

IR (neat): 2955, 2928, 1659, 1640, 1453, 1396, 1285, 1236, 1098, 680 cm$^{-1}$. $^1$H NMR (CDCl$_3$): δ=0.85 (d, J=7.0 Hz, 3 H, CH$_3$), 1.51-1.63 (m, 1 H, CH$_a$H$_b$), 1.71-1.78 (m, 1 H, CH$_a$H$_b$), 1.81 (quint, J=1.0 Hz, 3 H, CH$_3$), 1.88 (dq, J=7.0, 1.0 Hz, 3 H, CH$_3$), 2.04-2.13 (m, 2 H, =CH—CH$_2$—CH$_2$), 2.53-2.68 (m, 1 H, =CH—CH—CH$_3$), 2.91 (ddd, J=12.0, 9.5, 2.5 Hz, 1 H, CH—CH—CH$_2$), 5.54 (dq, J=10.0, 2.0 Hz, 1 H, =CH—CH), 5.61-5.69 (m, 1 H, =CH—CH$_2$), 6.73-6.83 (m, 1 H, CH$_3$—CH=). $^{13}$C NMR (CDCl$_3$): δ=11.2 (q), 14.8 (q), 20.1 (q), 25.1 (t), 27.4 (t), 32.5 (d), 47.5 (d), 125.0 (d), 133.2 (d), 136.7 (d), 138.5 (s), 205.2 (s). MS: m/z (%)=29 (11), 39 (14), 55 (53), 83 (100), 95 (8), 110 (2), 163 (5), 178 (4) [M$^+$].

Odour description: agrestic, dark fruity, berries, plum, Cyprisate (methyl 1,4-dimethylcyclohexanecarboxylate).

EXAMPLE 9

Perfume Examples

A series of perfumes was prepared according to the following formulae. The numbers signify parts by weight:

First, a base perfume was prepared, according to the following formula

| | |
|---|---|
| BENZYL ACETATE EXTRA | 10 |
| BENZYL SALICYLATE | 150 |
| CINNAMIC ALCOHOL SYNTHETIC | 1 |
| CITRONELLOL EXTRA (3,7-dimethyloct-6-en-1-ol) | 30 |
| CYCLOHEXAL(4-(4'-hydroxy-4'-methylpentyl)cyclohex-3-ene-1-carbaldehyde) | 60 |
| DIPROPYLENE GLYCOL | 49.1 |
| ETHYL LINALOOL | 20 |
| EUGENOL RECTIFIED | 20 |
| GALAXOLIDE (1,3,4,6,7,8-hexahydro-4,6,6,7,8,8-hexamethylcyclopenta[g]-2-benzopyran) | 45 |
| GARDENOL (1-phenylethyl acetate) | 4 |
| GERANYL ACETATE ([(2E)-3,7-dimethylocta-2,6-dienyl]acetate) | 15 |
| HEDIONE (methyl 3-oxo-2-pentylcyclopentaneacetate) | 30 |
| HELIOTROPINE CRYSTALS (1,3-benzodioxole-5-carbaldehyde) | 45 |
| HEXENYL-3-CIS SALICYLATE FINE | 30 |
| HYDROXYCITRONELLAL SYNTHETIC (7-hydroxy-3,7-dimethyloctanal) | 7 |
| INDOLE PURE (1H-indole) | 0.4 |
| IONONE BETA (4-(2',6',6'-trimethylcyclohexen-1'-yl)but-3-en-2-one) | 65 |
| IRISONE ALPHA ((E)-4-(2',6',6'-trimethyl-1'-cyclohex-2'-enyl)but-3-en-2-one) | 15 |
| ISO E SUPER (1-(2',3',8',8'-tetramethyl-1',3',4',5',6',7'-hexahydronaphthalen-2'-yl)ethanone) | 145 |
| LILIAL (3-(4'-tert-butylphenyl)butanal) | 120 |
| LINALOOL SYNTHETIC (3,7-dimethylocta-1,6-dien-3-ol) | 15 |
| LINALYL ACETATE SYNTHETIC (3,7-dimethylocta-1,6-dien-3-yl acetate) | 30 |
| LINDENOL (2-(4'-methyl-1'-cyclohex-3'-enyl)propan-2-ol) | 5 |
| PHENYL ETHYL ALCOHOL | 20 |
| RADJANOL ((E)-2-ethyl-4-(2',2',3'-trimethyl-1'-cyclopent-3'-enyl)but-2-en-1-ol) | 6 |
| TAGETES OIL EXTRA | 1 |
| THIBETOLIDE (16-oxacyclohexadecan-1-one) | 20 |
| VANILLIN (4-hydroxy-3-methoxy-benzaldehyde) | 1.5 |

To this base perfume, the following ingredients, were added, to provide 5 perfume compositions, labelled A, B, C, D and E. Total parts by weight of the 5 perfumes was 1000.

| PERFUME | A | B | C | D | E |
|---|---|---|---|---|---|
| Compound from Example 1 | | 2 | | | 20 |
| Compound from Example 2 | | | 2 | | |
| trans-compound from Example 3 [*] | | | | 2 | 2 |
| damascone delta | 2 | | | | 2 |
| DPG | 38 | 38 | 38 | 38 | 18 |
| Total | 1000 | 1000 | 1000 | 1000 | 1000 |

[*] (2E,6'R*,7'S*)-2-Methyl-1-(7'-methylspiro[4.5]dec-8'-en-6'-yl)but-2-en-1-one The perfumes were assessed by trained perfumers, and characterised as follows:

Perfume A—fruity, rosy character

Perfume B—similar to Perfume A, but with a slightly less fresh mint contribution Perfume C—similar in freshness to Perfume A, but a fruity agrestic twist Perfume D—similar to Perfume A, but with a lingering rosy effect, especially noticeable on dry skin Perfume E—similar to Perfume A, but possessing a stronger, rounder, more balanced and overall more pleasant odour. This is because it is possible to use considerably more of the compound of Example 1 (ten times in this instance), than is possible with Damascone™ compounds, because of the lack of skin sensitisation. This quantity is far in excess of the maximum proportion proposed by the guidelines of IFRA (International Fragrance Asssociation). The lack of skin sensitisation is demonstrated in Examples 12 and 13 hereinunder.

EXAMPLE 10

Perfume Examples in Fabric Conditioner

A base perfume was prepared according to the following formula (numbers signify parts by weight):

| | |
|---|---|
| AMBROFIX ((3aR,5aS,9aS,9bR)-3a,6,6,9a-tetramethyl-2,4,5,5a,7,8,9,9b-octahydro-1H-benzo[e][1]benzofuran) | 6 |
| BOURGEONAL (3-(4'-tert-butylphenyl)propanal) | 40 |
| COSMONE ((5E)-3-methylcyclotetradec-5-en-1-one) | 20 |
| FLORHYDRAL (3-(3'-propan-2'-ylphenyl)butanal) | 30 |
| FRESKOMENTHE (2-butan-2-ylcyclohexan-1-one) | 100 |
| HEDIONE | 180 |
| ISO E SUPER | 30 |

-continued

| | |
|---|---|
| LINALOOL SYNTHETIC | 100 |
| MEFROSOL (3-methyl-5-phenylpentan-1-ol) | 100 |
| MENTHANYL ACETATE (2-(4'-methylcyclohexyl)propan-2-yl acetate) | 100 |
| NEROLIONE (1-(3'-methyl-2'-benzofuran-1'-yl)ethanone) @ 10% in DPG | 2 |
| PINOACETALDEHYDE (3-(7',7'-dimethyl-4'-bicyclo[3.1.1]hept-3'-enyl)propanal) | 20 |
| PRUNOLIDE (5-pentyloxolan-2-one) | 6 |
| RADJANOL SUPER ((E)-2-ethyl-4-(2',2',3'-trimethyl-1'-cyclopent-3'-enyl)but-2-en-1-ol) | 40 |
| ROSSITOL (1-methyl-3-(2'-methylpropyl)-cyclohexanol) | 100 |
| SILVANONE SUPRA (cyclopentadecanone/cyclohexadecanone mixture) | 100 |
| YLANG YLANG OIL | 6 |

The base perfume is a fresh, watery, floral, musky accord specifically formulated for use in fabric conditioners.

To this base perfume, was added the following ingredients, to make Perfumes G, H and I. (Perfume F is the base perfume with only an addition of DPG to make the respective weight proportions equal.)

| PERFUME | F | G | H | I |
|---|---|---|---|---|
| Compound from Example 1 | | 20 | | |
| Compound from Example 2 | | | 20 | |
| trans-compound from Example 3 [*] | | | | 20 |
| DPG | 20 | | | |
| Total | 1000 | 1000 | 1000 | 1000 |

[*] (2E,6'R*,7'S*)-2-Methyl-1-(7'-methylspiro[4.5]dec-8'-en-6'-yl)but-2-en-1-one These perfumes were added at 1% (wt) to a fabric conditioner of the following formula in which the numbers represent parts by weight

| | |
|---|---|
| Esterquat cationic surfactant[1] | 12.00 |
| Soft water | 86.65 |
| Calcium chloride | 0.30 |
| Antimicrobial[2] | 0.03 |
| Preservative[3] | 0.02 |
| Detergent alcohol[4] | 1.00 |

[1] DEHYQUART ™ AU 57 ex BASF
[2] 2-bromo-2-nitropropane (BRONIDOX ™ L ex Cognis)
[3] benzisothiazolinone (PROXEL ™ GXL ex Lonza)
[4] Ethoxylated C12-15 alcohol (NEODOL ™ 25-7 ex Shell)

This was used to wash a load of 3 towels, as follows:
Machine: Miele Navitronic W3985.
Washing cycle duration: 16 minutes
Water temperature: room
Spin-dry: 1200 rpm.
Fabric conditioner added: 35 g The towels were assessed by trained perfumers, and the results were as follows:
Perfume F—fresh, watery, floral, musky
Perfume G—adds to Perfume F's qualities an additional clear, fruity, rosy twist, giving it a more pronounced feminine accord with an undertone of gourmand cooked apple
Perfume H—adds to Perfume F's qualities a fresh mintiness and natural agrestic facette.
Perfume I—adds to Perfume F's qualities a pleasant fruity, rosy character, especially noticeable on dry cloth.

EXAMPLE 11

Preparation and Application of a Precursor for a Non-Sensitizing Damascone™-Type Perfumery Ingredient (2E,1'R*,2'S*)-2-Methyl-(2',6',6'-trimethylcyclohex-3'-en-1'-yl)but-2-en-1-one (cf. Example 1, 1.00 g, 4.85 mmol) and dodecane-1-thiol (930 mg, 4.59 mmol) were dissolved in THF (10 ml), and 1,8-diazabicyclo[5.4.0]undec-7-ene (740 mg, 4.86 mmol) was added. The resulting solution was stirred at room temperature for 22 h, then poured into ice-cold 2 M aqueous HCl-solution (40 ml). The product was extracted with methyl t-butyl ether (2×50 mL). The combined organic layers were washed with brine, dried over $MgSO_4$, and concentrated under reduced pressure. The resulting residue was purified by flash chromatography (90 g silica gel, hexane/methyl t-butyl ether, 100:1) to yield the product as a colourless oil (750 mg, 38%) as a mixture of diastereomers.

MS for diastereomers 11.1-11.5 (area-% by GC): Diastereomer 9.1 (33%): m/z (%)=29 (22), 41 (29), 55 (51), 83 (100), 132 (30), 229 (42), 257 (27), 285 (6), 408 (<1, M$^+$); diastereomer 11.2 (27%): m/z (%)=29 (10), 41 (20), 55 (34), 83 (100), 123 (16), 229 (24), 257 (14), 285 (3), 408 (<1, M$^+$); diastereomer 11.3 (11%): m/z (%)=29 (18), 41 (32), 55 (51), 83 (100), 123 (29), 229 (48), 257 (24), 285 (5), 408 (<1, M$^+$); diastereomer 11.4 (11%): m/z (%)=29 (14), 41 (29), 55 (33), 69 (18), 83 (100), 123 (16), 206 (7), 243 (30), 257 (4), 408 (<1, M$^+$); diastereomer 11.5 (8%): m/z (%)=29 (14), 43 (32), 55 (55), 69 (18), 83 (100), 123 (34), 229 (56), 257 (32), 285 (8), 408 (<1, M$^+$).

For the demonstration of the long-lasting release properties of a non-sensitizing Damascone™-like fragrance ingredient, two fabric conditioner samples A and B were prepared as follows:

To an unperfumed fabric conditioner base as described in Example 10 (15.9 g) was added a mixture of dipropylene glycol (144 mg) and either (2E,1'R*,2'S*)-2-methyl-(2',6',6'-trimethylcyclohex-3'-en-1'-yl)but-2-en-1-one (cf. Example 1, 16.0 mg, Sample A) or the precursor as above prepared (16.0 mg, Sample B).

Two standard wash/rinse cycles were carried out contemporarily, each with a 1 kg load of cotton terrycloth towels in European front-loading washing machines, using an unperfumed powder detergent (35.0 g) for the wash cycles and the above described fabric conditioner samples A and B for the rinse cycles.

The odour intensity of the towels was judged by a panel of 6 expert assessors on a scale of 0 (odourless) to 5 (very strong) at wet stage and after 4 days (1 day line dry, then folded and left at room temperature in ambient air). The results are summarized in the following Table.

| Sample | mean intensity score on wet | Paired Student's t-test (wet) | mean intensity score after 4 days | Paired Student's t-test (4 days) |
|---|---|---|---|---|
| A (free odorant) | 2.5 | p = 0.6 | 1.5 | p = 0.008 |
| B (precursor) | 2 | | 2.2 | |

The results show that at wet stage, the free odorant imparted a slightly higher odour intensity to the towels, the difference was however not significant. After 4 days, the towels rinsed with the precursor containing fabric conditioner sample had a significantly higher intensity score. The odour quality was described as fruity, floral, Damascone™-like.

EXAMPLE 12

Demonstration of Reduced Sensitisation of Compounds

Compounds were tested using the commercial KeratinoSens™ assay for skin sensitization.

The compound of Example 1 ("Example 1") was compared with Damascone delta™.

Figure 1:
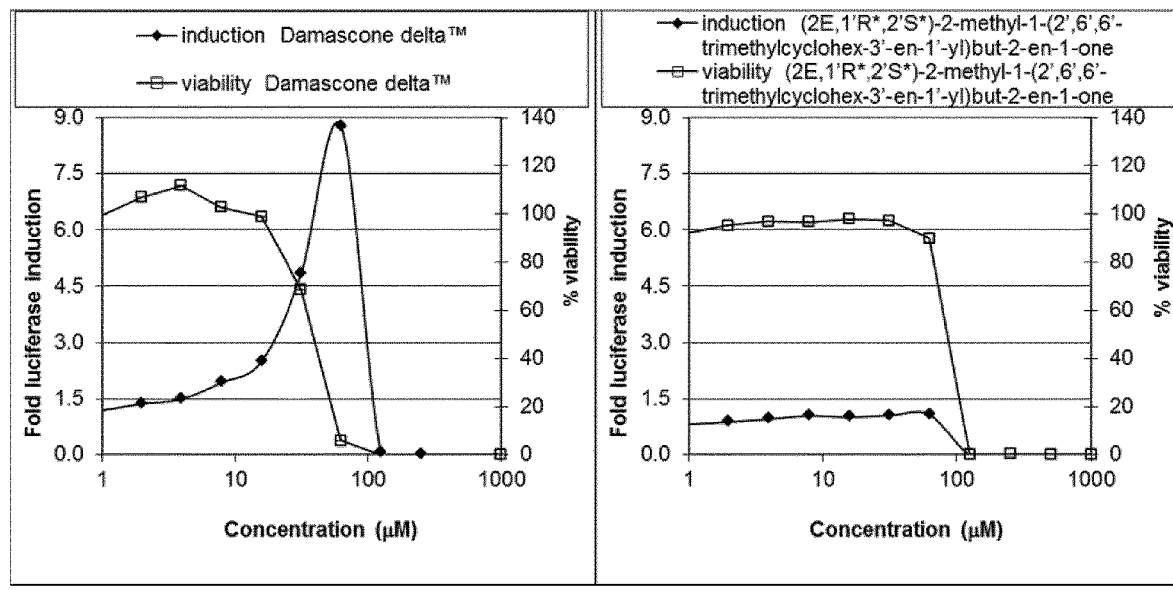
FIG. 1 shows the gene-induction and cell viability curves for Damascone delta™ and Example 1, in which the black diamonds indicate the induction of the luciferase activity and the open squares Cellular viability.

Example 1 did not induce luciferase activity above the 1.5-fold threshold, and is thus rated as non-sensitizing by this assay. Damascone delta™ on the other hand clearly induces the luciferase gene already at 4 micromolar, indicating it is a significantly sensitizing compound and maximal gene induction reaches 8.7-fold over control. These results show that Example 1 can be used in perfume formulations for reduced sensitization risk to the consumer. Table 1 shows the results of other compounds according to this disclosure, as compared with Damascone delta™. With the exception of example 6, none of the inventive compounds induced the gene above the threshold of 1.5-fold at non-cytotoxic concentrations, while the maximal gene induction was at 8.7 for Damascone delta™. A marginal gene induction (1.67-fold at 125 µM only) was noted for example 6. This indicates that all inventive compounds have a strongly reduced sensitization potential as compared to Damascone delta™.

| | Imax (fold maximal gene induction) | Concentration for 1.5-fold gene induction (EC 1.5 in µM) | Concentration for 50% Cytotoxicity (in µM) |
|---|---|---|---|
| Damascone delta ™ | 8.77 | 3.96 | 40.47 |
| Compound of Example 1 | 1.09 | n.i. | 90.3 |
| Compound of Example 2 | 1.28 | n.i. | 112.1 |
| (2E,6'R*,7'R*)-2-Methyl-1-(7'-methylspiro[4.5]dec-8'-en-6'-yl)but-2-en-1-one (Example 3) | 1.12 | n.i. | 48.8 |
| (2E,6'R*,7'S*)-)-2-Methyl-1-(7'-methylspiro[4.5]dec-8'-en-6'-yl)but-2-en-1-one (Example 3) | 1.19 | n.i. | 21.4 |
| Compound of Example 4 | 1.36 | n.i. | 176.2 |
| Compound of Example 5 | 1.51 | Induction only below 70% viability | 77.5 |
| Compound of Example 6 | 1.64 | 48.8 | 89.3 |
| (2E,1'R*,2'S*)-2-Methyl-1-(2'-methylcyclohex-3'-en-1'-yl)but-2-en-1-one (Example 7) | 1.26 | n.i. | 339.8 |
| (2E,1'R*,2'R*)-2-Methyl-1-(2'-methylcyclohex-3'-en-1'-yl)but-2-en-1-one (Example 8) | 1.35 | n.i. | 316.4 | n.i. no induction above threshold of 1.5

EXAMPLE 13

Compounds Tested in the a Peptide Reactivity Assay for Skin Sensitization

A second method to determine allergenic potential of chemicals is the DPRA direct peptide assay (OECD TG 442c). It is based on the fact that allergenic chemicals must react with a peptide/protein in order to be immunogenic.

A peptide reactivity assay (A. Natsch, H. Gfeller, *Toxicol. Sci* 2008, 106, 464-478) was conducted similarly to the DPRA assay: The test chemicals were dissolved to a final concentration of 4 mM in acetonitrile and 250 µl of this solution were added to 2 ml HPLC vials. The test peptide Cor1C-420 with the sequence Ac-NKKCDLF (Genscript Inc., Piscataway, N.J., USA), was dissolved at 0.133 mM in 20 mM phosphate buffer at pH 7.5, and 750 µl of this solution were added to each test vial (final concentrations: 1 mM of test chemical and 0.1 mM of peptide in 25% acetonitrile; ratio 1:10 as in the DPRA assay). The samples were incubated for 1-24 h at 37° C. and at regular intervals they were analysed by LC-MS analysis on a VELOS PRO Mass spectrometer (Thermo SCIENTIFIC, San Jose, Calif., U.S.A.) operated in the ESl(+) mode. The temperature of the capillary was kept at 275° C. Mass spectra were recorded from 200-2000 amu. A ZORBAX Eclipse XDB-C18 column, 2.1 mm ID, 150 mm, 5-Micron (Agilent Technologies) was used. The mobile phase consisted of $H_2O$ (A) and methanol (B) each containing 0.1% formic acid (v/v). The solvent flow was 250 µl/min and the following gradient (ratio A: B) was used: 0 min, 95:5; 2 min, 40:60; 10 min, 2:98; 12 min, 2:98. The integration was performed with Xcalibur Quan Browser™.

Figure 2:
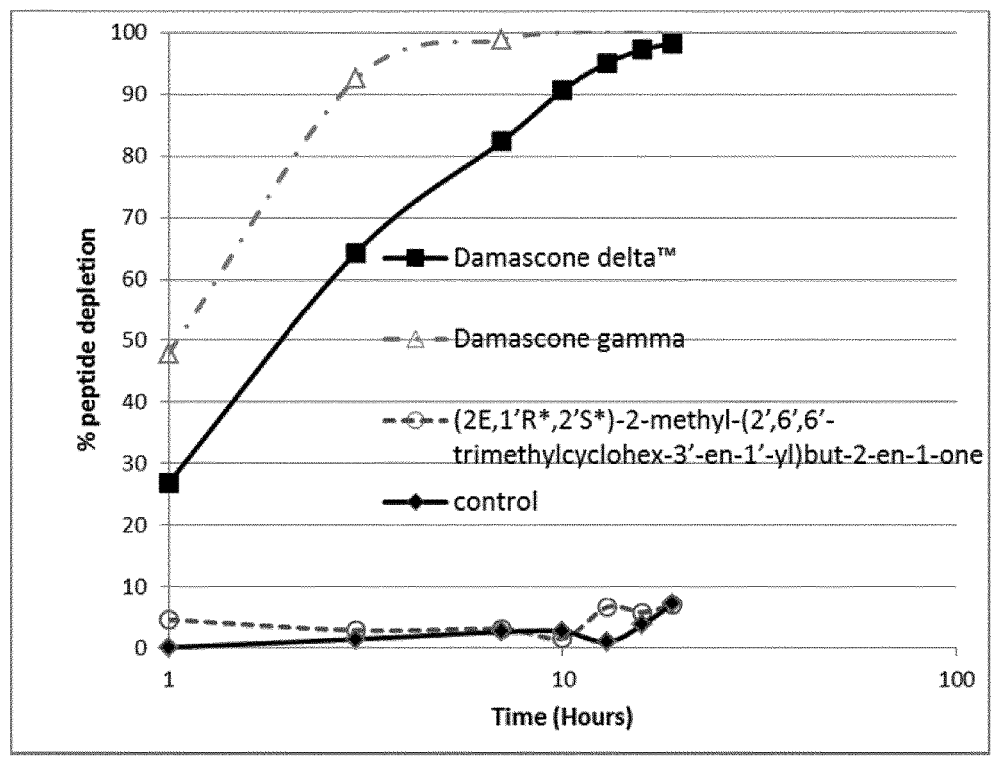
FIGS. 2 (peptide depletion) and 3 (adduct formation on a logarithmic scale) compare the peptide reactivity of two commercial damascones with the compound of Example 1 ("Example").
Figure 3:
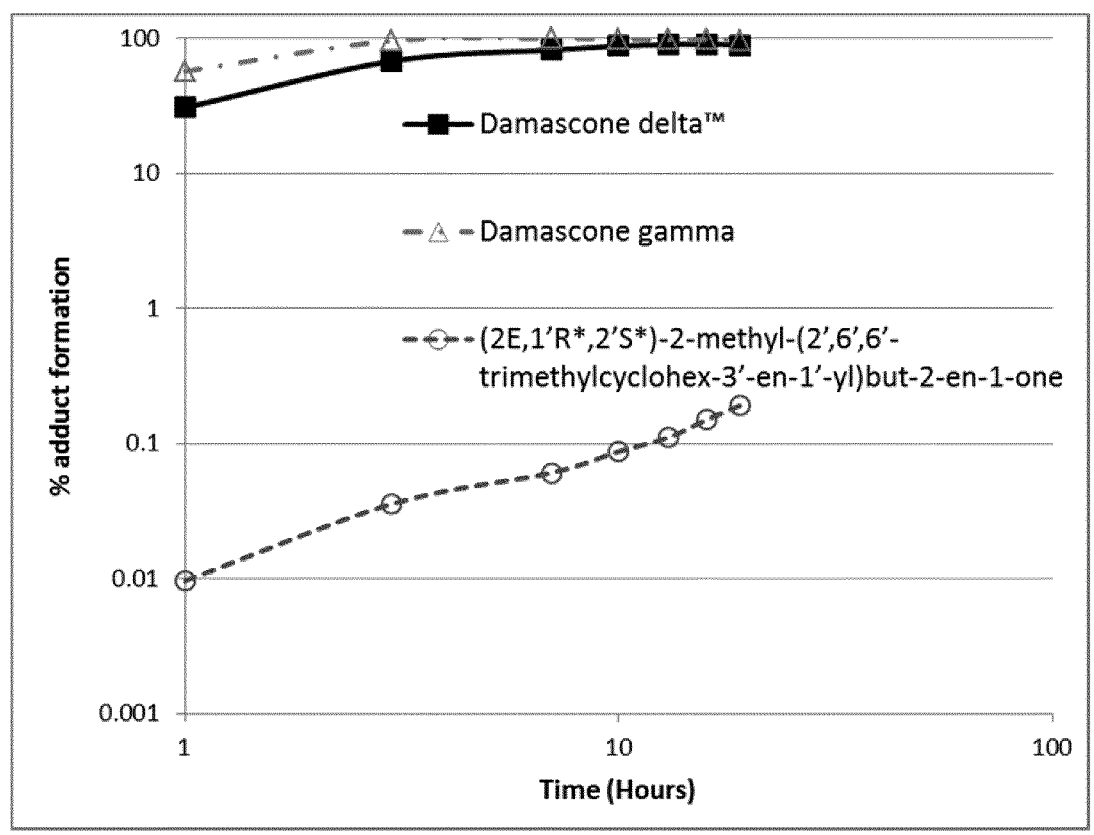

Two endpoints are measured with this assay:
a) Depletion of the parent peptide. The mass of the protonated parent peptide is measured and the corresponding peak integrated (% depletion; FIG. 2). Depletion of the parent peptide is indicative of reactivity and is described as endpoint in OECD guideline 442c.
b) Formation of modified peptides. The specific ion trace for a new adduct with the mass of the test chemical added to the test peptide is extracted, and the peak of the peptide-adduct is integrated (FIG. 3). Peptide adduct formation is a particular sensitive endpoint to determine reactive, and thus allergenic nature of compounds.

FIGS. 2 (peptide depletion) and 3 (adduct formation on a logarithmic scale) compare the 5 peptide reactivity of two commercial damascones with the compound of Example 1 ("Example 1"). After 1 h, Example 1 produces 3200-fold lower levels of peptide adducts as compared to Damascone delta™, and no significant peptide depletion is noted over the 24 h experiment, indicating a dramatic and unexpected reduction of reactivity (and thus allergenicity) for Example 1.

The invention claimed is:

1. A compound of the formula (I)

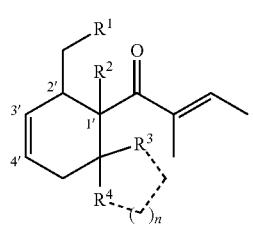

(I)

in which, independently,
$R_1$ is selected from H, and methyl;
$R_2$ is selected from H, and methyl;
$R_3$ is selected from H, methyl and ethyl;
$R_4$ is selected from H, methyl and ethyl;
or $R_3$ and $R4$ together form a ring in which n is 1 or 2.

2. The compound according to claim 1, wherein both $R^1$ and $R^2$ are hydrogen.

3. The compound according to claim 2, wherein $R^4$ is selected from methyl and ethyl, or wherein $R^3$ and $R^4$ together form a cyclopentyl ring (n=1).

4. The compound according to claim 3 selected from the group consisting of
(2E,1'R*,2'S*)-2-methyl-1-(2',6',6'-trimethylcyclohex-3'-en-1'-yl)but-2-en-1-one,
(2E,1'R*,2'R*)-2-methyl-1-(2',6',6'-trimethylcyclohex-3'-en-1'-yl)but-2-en-1-one,
(2E,6'R*,7'S*)-2-methyl-1-(7'-methylspiro[4.5]dec-8'-en-6'-yl)but-2-en-1-one,
(2E,6'R*,7'R*)-2-methyl-1-(7'-methylspiro[4.5]dec-8'-en-6'-yl)but-2-en-1-one,
(2E)-1-(2',6'-dimethylcyclohex-3'-en-1'-yl)-2-methylbut-2-en-1-one,
(2E)-1-(6'-ethyl-2'-methylcyclohex-3'-en-1'-yl)-2-methylbut-2-en-1-one,
(2E)-2-methyl-1-(1',2',6'-trimethylcyclohex-3'-en-1'-yl)but-2-en-1-one,
(2E,1'R*,2'S*)-2-methyl-1-(2'-methylcyclohex-3'-en-1'-yl)but-2-en-1-one, and
(2E,1'R*,2'R*)-2-methyl-1-(2'-methylcyclohex-3'-en-1'-yl)but-2-en-1-one.

5. (2E,1'R*,2'S*)-2-methyl-1-(2',6',6'-trimethylcyclohex-3'-en-1'-yl)but-2-en-1-one.

6. A method comprising using in a fragrance composition or incorporating in a fragrance application as a fragrance ingredient, a compound or compounds of formula (I) according to claim 1.

7. A fragrance composition comprising a compound according to claim 1 and at least one other fragrance ingredient.

8. A perfumed product comprising a perfumed product base and at least one compound according to claim 1.

9. The perfumed product according to claim 8, selected from fine perfumery, fabric care, household products, beauty and personal care products and air care products.

10. A precursor capable of generating a compound according to Formula (I) as defined in claim 1, having the Formula (II):

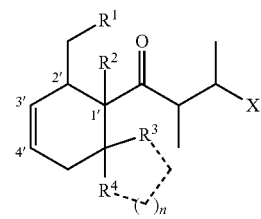

(II)

in which X is selected from $SR^5$, $NHR^6$ and $NR^6R^7$; $R^5$, $R^6$ and $R^7$ being selected from linear or branched $C_1$-$C_{15}$ alkyl, a $C_3$-$C_8$ cycloalkyl or an aryl substituent, both optionally substituted with linear or branched $C_1$-$C_7$ alkyl groups or, in the case of $NR^6R^7$, $R^6$ and $R^7$, together with the nitrogen atom to which they are attached, form part of a polymeric entity.

11. A method of providing in a fragrance application a compound of Formula (I) according to claim 1, comprising
(i) preparing a precursor compound according to Formula II

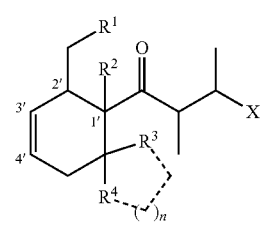

(II)

in which X is selected from $SR^5$, $NHR^6$ and $NR^6R^7$; $R^5$, $R^6$ and $R^7$ being selected from linear or branched $C_1$-$C_{15}$ alkyl, a $C_3$-$C_8$ cycloalkyl or an aryl substituent, both optionally substituted with linear or branched $C_1C_7$ alkyl groups or, in the case of $NR^6R^7$, $R^6$ and $R^7$, together with the nitrogen atom to which they are attached, form part of a polymeric entity;

(ii) adding the precursor compound of Formula II to an application; and (iii) subjecting the application to conditions that will result in the generation of a compound according to Formula (I).

12. A method comprising adding in a fragrance application, a compound according to Formula II

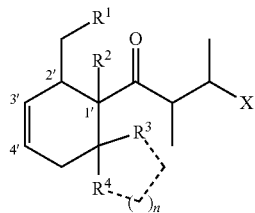

(II)

in which X is selected from SR$^5$, NHR$^6$ and NR$^6$R$^7$; R$^5$, R$^6$ and R$^7$ being selected from linear or branched C$_1$-C$_{15}$ alkyl, a C$_3$C$_8$ cycloalkyl or an aryl substituent, both optionally substituted with linear or branched C$_1$-C$_7$ alkyl groups or, in the case of NR$^6$R$^7$, R$^6$ and R$^7$, together with the nitrogen atom to which they are attached, form part of a polymeric entity; for the in situ generation of a compound according to claim 1.

13. A method of providing in a fragrance application a fruity-floral fragrance note with reduced skin sensitization, comprising the addition to a fragrance application base of a compound according to claim 1.

14. The method according to claim 13, wherein both R$^1$ and R$^2$ are hydrogen.

15. The method according to claim 14, wherein R$^4$ is selected from methyl and ethyl, or wherein R$^3$ and R$^4$ together form a cyclopentyl ring (n=1).

16. The method according to claim 15, in which the compound is selected from the group consisting of:
    (2E,1'R*,2'S*)-2-methyl-1-(2',6',6'-trimethylcyclohex-3'-en-1'-yl)but-2-en-1-one,
    (2E,1'R*,2'R*)-2-methyl-1-(2',6',6'-trimethylcyclohex-3'-en-1'-yl)but-2-en-1-one,
    (2E,6'R*,7'S*)-2-methyl-1-(7'-methylspiro[4.5]dec-8'-en-6'-yl)but-2-en-1-one,
    (2E,6'R*,7'R*)-2-methyl-1-(7'-methylspiro[4.5]dec-8'-en-6'-yl)but-2-en-1-one,
    (2E)-1-(2',6'-dimethylcyclohex-3'-en-1'-yl)-2-methylbut-2-en-1-one,
    (2E)-1-(6'-ethyl-2'-methylcyclohex-3'-en-1'-yl)-2-methylbut-2-en-1-one,
    (2E)-2-methyl-1-(1',2',6'-trimethylcyclohex-3'-en-1'-yl)but-2-en-1-one,
    (2E,1'R*,2'S*)-2-methyl-1-(2'-methylcyclohex-3'-en-1'-yl)but-2-en-1-one, and
    (2E,1'R*,2'R*)-2-methyl-1-(2'-methylcyclohex-3'-en-1'-yl)but-2-en-1-one.

17. The method according to claim 16, in which the compound is (2E,1'R*,2'S*)-2-methyl-1-(2',6',6'-trimethylcyclohex-3'-en-1'-yl)but-2-en-1-one.

* * * * *